US006928313B2

(12) United States Patent
Peterson

(10) Patent No.: US 6,928,313 B2
(45) Date of Patent: Aug. 9, 2005

(54) SYSTEM AND METHOD FOR ACCESSING THE CORONARY SINUS TO FACILITATE INSERTION OF PACING LEADS

(75) Inventor: Eric D. Peterson, Fremont, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 183 days.

(21) Appl. No.: 10/351,718

(22) Filed: Jan. 27, 2003

(65) Prior Publication Data

US 2004/0147826 A1 Jul. 29, 2004

(51) Int. Cl.[7] ................................................. A61B 5/04
(52) U.S. Cl. ....................................................... 600/374
(58) Field of Search ................................. 600/373–375, 600/433–435; 604/96.01, 104, 264; 606/41, 46; 128/898

(56) References Cited

U.S. PATENT DOCUMENTS

| 4,917,104 | A | 4/1990 | Rebell |
| 4,983,165 | A | 1/1991 | Loiterman |
| 5,179,961 | A | 1/1993 | Littleford et al. |
| 5,571,161 | A | 11/1996 | Starksen |
| 5,775,327 | A | 7/1998 | Randolph et al. |
| 5,807,324 | A | 9/1998 | Griffin, III |
| 5,971,983 | A | * 10/1999 | Lesh ............................ 606/41 |
| 5,993,424 | A | 11/1999 | Lorenzo et al. |
| 6,021,340 | A | 2/2000 | Randolph et al. |
| 6,029,671 | A | * 2/2000 | Stevens et al. .............. 128/898 |
| 6,122,552 | A | 9/2000 | Tockman et al. |
| 6,126,635 | A | 10/2000 | Simpson et al. |
| 6,287,319 | B1 | 9/2001 | Aboul-Hosn et al. |
| 6,290,697 | B1 | 9/2001 | Tu et al. |
| 6,416,511 | B1 | 7/2002 | Lesh et al. |
| 6,733,500 | B2 | * 5/2004 | Kelley et al. .................. 606/41 |
| 2003/0204138 | A1 | * 10/2003 | Choi ........................... 600/434 |

FOREIGN PATENT DOCUMENTS

WO    WO 01/00268 A1    4/2001

* cited by examiner

*Primary Examiner*—George Manuel
(74) *Attorney, Agent, or Firm*—Crawford Maunu PLLC

(57) ABSTRACT

A guiding catheter system employs an outer jacket with one or more inflation lumens provided along the length of the jacket. The lumens are in fluid communication with one or more fluted balloons mounted at a distal end of the outer jacket. A torquable stylet is movably disposed within an open lumen of the outer jacket. A guidewire is movably disposed in an open lumen of the torquable stylet. The outer jacket can be provided with break-away features allowing the jacket to be peeled off of a pacing lead.

25 Claims, 6 Drawing Sheets

Section 4-4

Section 4-4

Section 4-4

Section 5-5

Section 5-5

Section 6-6

Section 8-8

SYSTEM AND METHOD FOR ACCESSING THE CORONARY SINUS TO FACILITATE INSERTION OF PACING LEADS

FIELD OF THE INVENTION

The invention relates generally to guiding catheter systems, and more particularly to guiding catheters for accessing the coronary sinus from the right atrium.

BACKGROUND OF THE INVENTION

Guiding catheters are instruments that allow a physician to locate and cannulate vessels in a patient's heart for performing various medical procedures, including venography and implanting of cardiac pacing devices. Cannulating heart vessels requires navigating a small diameter, flexible guide through convoluted vasculature into a heart chamber, and then into a destination heart vessel. Once the destination heart vessel is reached, the catheter acts as a conduit for insertion of payloads into the vessel.

The major goal of a guiding catheter procedure is to find and cannulate a vessel of interest in the least amount of time. Finding and cannulating the coronary sinus, for example, can become a time consuming, trial and error procedure even in a healthy patient. Patients exhibiting symptoms of advanced heart disease can have blockages or deformations of heart structure, further complicating the task of locating the opening (ostium) of the coronary sinus from the right atrium.

A pre-shaped guiding catheter has traditionally been used to locate the destination vessel. A fixed shape catheter is adequate in many cases where the pathway is not significantly convoluted and the pathway does not deviate significantly between patients. In situations where structural anomalies or significant variations exist, use of a fixed shape catheter may require that the clinician stock multiple size and shapes of catheters to account for potential variations. Further, it may be necessary that a fixed shaped catheter be swapped out during an implantation procedure with a different shaped catheter due to difficulties in maneuvering.

In some cases, it is desired to have the ability to dynamically shape a distal end of the catheter. Guiding catheters sometimes utilize steering tendons or wires to assist in directing the distal end of the catheter during cannulation. Although this method can be effective, the wires and associated hardware take up valuable space in the guide lumen of the catheter. Also, the relatively long and potentially convoluted passageways traversed by guide catheters lead to complication in the use of steering wires, including pull friction and mechanical backlash.

There is a need for a guide catheter with a maneuverable distal end that does not utilize pull wires. The present invention fulfills these and other needs, and addresses other deficiencies of prior art implementations and techniques.

SUMMARY OF THE INVENTION

To overcome the limitations in the prior art described above, and to overcome other limitations that will become apparent upon reading and understanding the present specification, the present invention discloses a steerable guiding catheter that can provide access to venous structures for medical procedures.

According to one embodiment of the present invention, a guiding catheter system for accessing a patient's heart includes an outer jacket having an open guide lumen, at least one inflation lumen provided along an exterior surface of the outer jacket, and at least one segment of a distal balloon fixably mounted at a distal portion of the outer jacket. The outer jacket can be configured to include a peel away feature provided along a longitudinal length of the outer jacket. The distal balloon is in fluid communication with the inflation lumen. One or more secondary balloons can be integrated into the inflation lumen, such that the secondary balloons are situated proximal to the distal balloon segment.

A stylet is disposed within the guide lumen of the outer jacket. The stylet is rotatable within the outer jacket along a longitudinal axis thereof. The stylet can be formed to include an open lumen dimensioned to receive a guidewire. The stylet can include a pre-formed curve at a distal portion of the stylet.

A guidewire is movably disposed within the open lumen of the stylet. The guidewire, in one configuration, is formed from a material such that a distal tip of the guidewire is substantially straight at ambient temperature and the distal tip assumes a shape of a loop at body temperature.

In accordance with another embodiment, a method of cannulating a destination blood vessel involves introducing an outer jacket and a stylet of a catheter system into an access vessel. The stylet is rotated within a guide lumen of the outer jacket so that a pre-formed bend on a distal end of the stylet deflects the outer jacket to steer a distal end of the outer jacket. A guidewire can be advanced through an open lumen of the stylet to engage the destination blood vessel with a distal end of the guidewire. A balloon attached to a distal portion of the outer jacket is inflated to engage a portion of the access vessel or the destination blood vessel with the outer jacket.

The method can further involve advancing the outer jacket over the guidewire after the distal end of the guidewire has engaged the destination blood vessel to seat the outer jacket in the destination blood vessel. The guidewire and stylet can be removed after seating the outer jacket in the destination blood vessel. An electrical medical lead can be advanced through the outer jacket for passage into or through the destination blood vessel or chamber, such as a left heart vessel or chamber.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
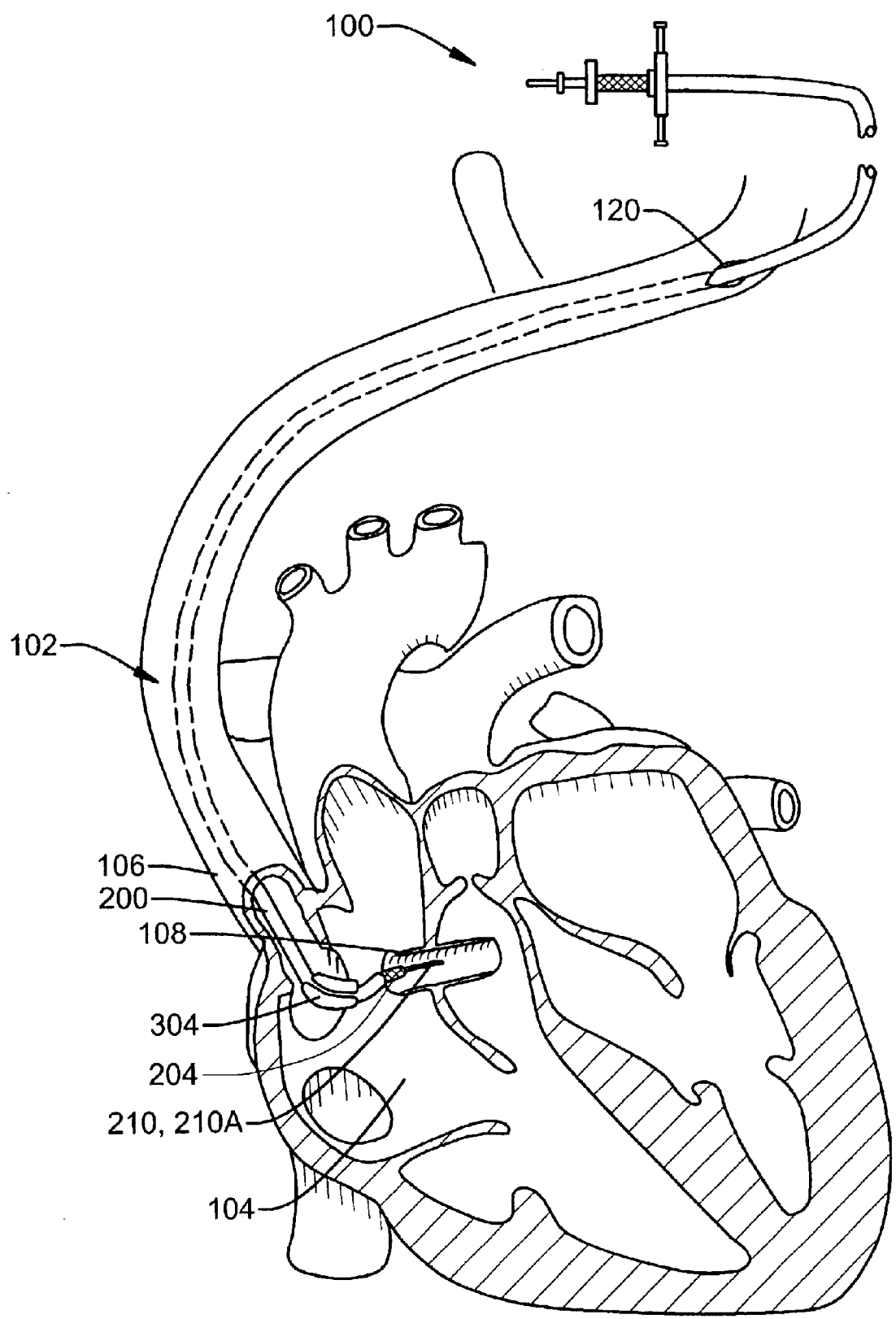
FIG. 1 is a cutaway view of a heart, showing a guiding catheter system according to an embodiment of the present invention deployed in the superior vena cava and right atrium.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In broad and general terms, a guiding catheter system according to concepts of the present invention employs an outer jacket with one or more inflation lumens provided along the length of the jacket. The lumens are in fluid communication with one or more balloons, typically fluted balloons, mounted at a distal end of the outer jacket. A torquable stylet is movably disposed within an open lumen of the outer jacket. The stylet can be formed to include a bend which imparts a deflection to the outer jacket for steering and manipulation purposes. The stylet can also be formed to include an open lumen dimensioned to receive a guidewire.

Referring now to FIG. 1, a guide catheter system, generally indicated by reference numeral 100, is shown deployed in the right atrium 104 of the heart. The guide catheter system 100 includes a shaft portion 102 adapted for traversal of blood vessels. As will be described hereinbelow, the catheter system 100 provides various advantageous features allowing improved access to various anatomical regions, and is particularly suited to accessing heart vessels. FIG. 1 shows the shaft portion 102 entering the right atrium 104 via the superior vena cava 106 and positioned to cannulate the coronary sinus 108.

Figure 2:
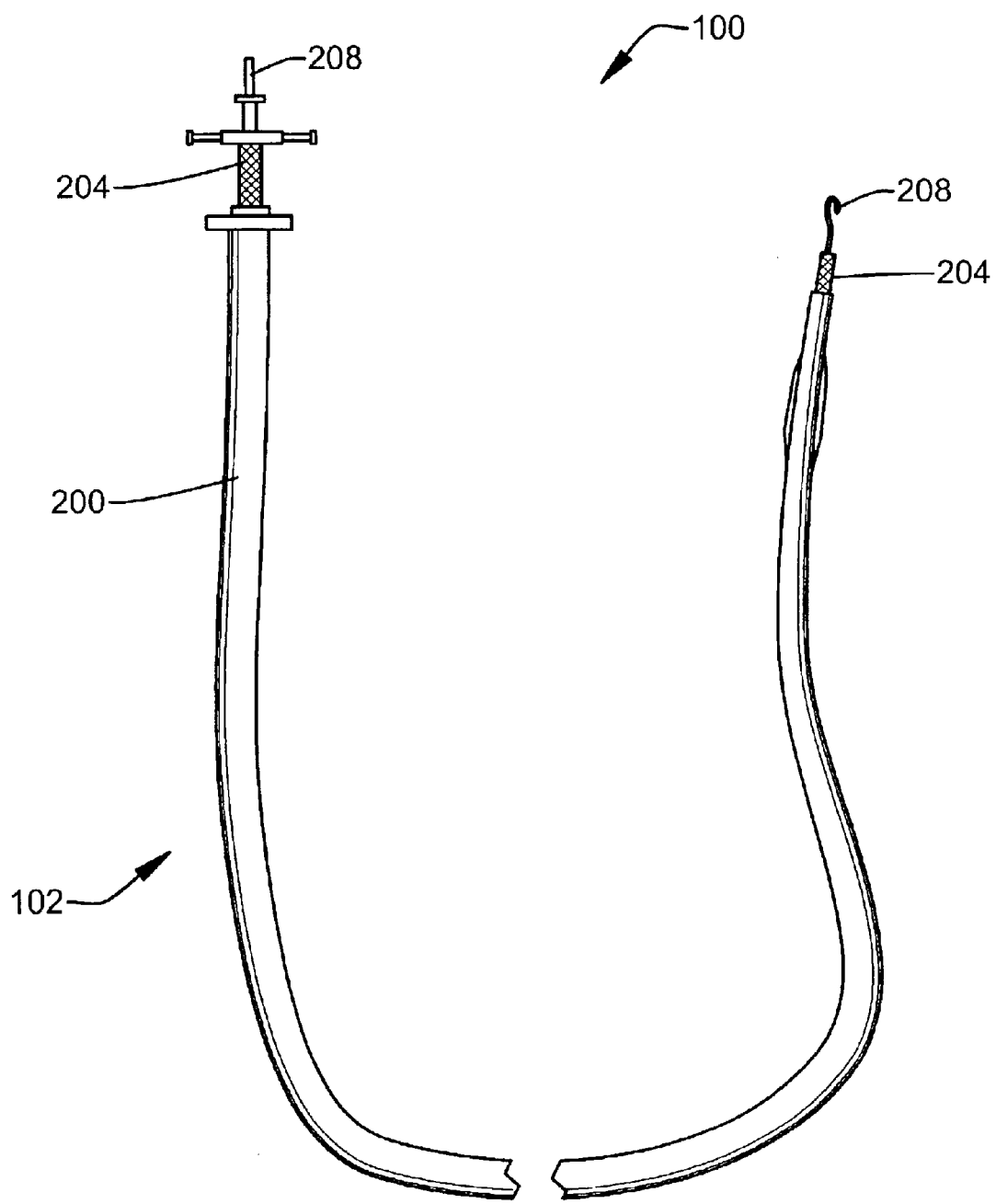
FIG. 2 is side view of a guide catheter assembly according to one embodiment of the present invention.

Turning now to FIG. 2, one embodiment of a catheter system 100 according to the present invention is illustrated, various features of which are shown in FIG. 1. A substantial portion of the shaft's exterior surface is covered by an outer jacket 200. The outer jacket 200 includes a guide lumen, which can movably receive a torquable stylet 204. The stylet 204 is similar in construction to a standard guiding catheter, having an open lumen and may also include a pre-shaped distal end. In certain applications, the stylet 204 need not include an open lumen. A guidewire 208 is movably disposed within the open lumen of the stylet 204. The guidewire 208 can be used to steer a distal end of the shaft portion 102, and can include attachments such as a sensor.

Figure 3:
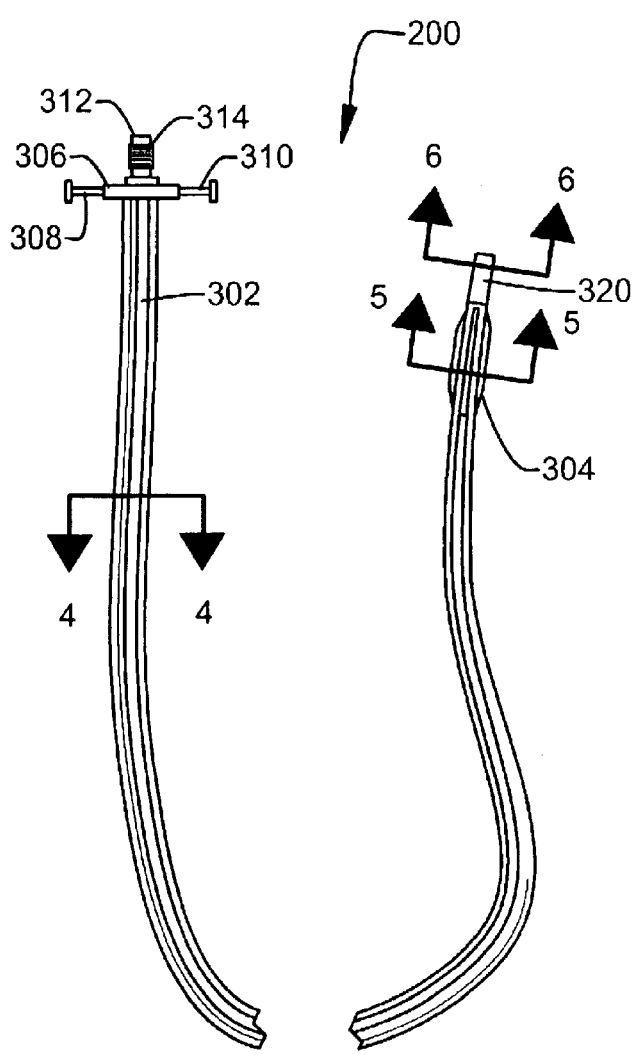
FIG. 3 is a side view of an outer jacket according to an embodiment of the present invention.

A more detailed view of the outer jacket 200 is shown in FIG. 3. The outer jacket 200 includes one or more inflation lumens 302 disposed along an outer surface of the jacket 200. The inflation lumens 302 are in fluid communication with one or more fluted balloons 304 situated at a distal portion of the jacket 200. The fluted balloon(s) 304 are inflatable to provide support to the shaft portion 200 and can also be used to occlude blood vessels.

At the other end of the outer jacket 200, a proximal hub 306 is attached. The hub 306 may include a flush port 308 in fluid communication with a guide lumen 400 of the jacket 200 (best seen in FIG. 4A) and a balloon inflation port 310 in fluid communication with the inflation lumens 302. A guide port 312 is also attached to the hub 306 in axial alignment with the outer jacket 200. The guide port 312 allows introduction of the stylet 204 into the outer jacket 200. The guide port 312 may also have a threaded portion 314 suitable for attachment of a device such as a rotating hemostatic valve (RHV).

The hub 306 and outer jacket 200 can be made with features allowing the outer jacket 200 to be peeled away in use. This is typically accomplished by making the hub 306 splittable and providing some type of peeling feature along the length of the outer jacket 200. Such peeling features can be formed in the outer jacket by forming pre-stress features (e.g., by notching or scoring) or by extruding the walls of the outer jacket 200 so that there are regions of varying wall thickness.

The outer jacket 200 is typically tapered so that the proximal end has a larger diameter than the distal end. The distal end of the outer jacket 200 may include a soft distal tip 320. The distal tip 320 can either be bonded separately or formed from a co-extrusion of the jacket 200.

Figure 4A:
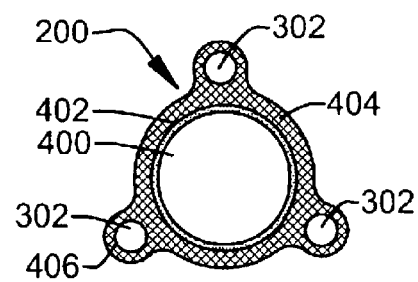
FIG. 4A is a cross sectional view of the outer jacket's proximal end corresponding to cross section 4—4 of FIG. 3.

The construction details of the outer jacket 200 are best seen in the cross sectional views of FIGS. 4A–6. FIG. 4A shows a proximal section of the outer jacket 200. In this example, three inflation lumens 302 are spaced around the outer surface of the outer jacket 200. The inflation lumens 302 are typically smaller than the guide lumen 400. An inner liner 402 surrounds the guide lumen 400. The inner liner 402 is preferably made from a relatively hard lubricious material such as HDPE. The guide lumen walls 404 and inflation lumen walls 406 can be formed from a single extruded piece of a softer material such as LDPE or Pebax 55D.

Figure 4B:
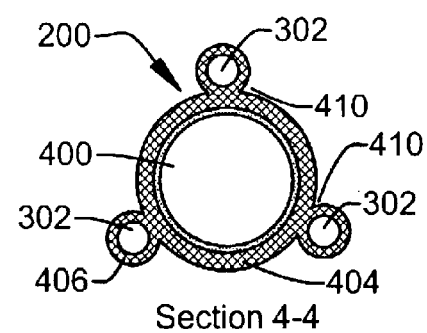
FIG. 4B is a cross sectional view of the outer jacket's proximal end corresponding to cross section 4—4 of FIG. 3 showing an alternate arrangement with a peel-away undercut.
Figure 4C:
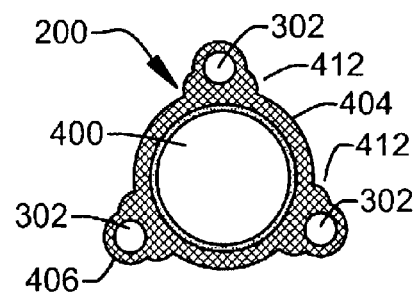
FIG. 4C is a cross sectional view of the outer jacket's proximal end corresponding to cross section 4—4 of FIG. 3 showing an alternate arrangement with a peel-away reinforcement.

FIG. 4B illustrates an inflation lumen layout similar to that shown in FIG. 4A, except that undercuts 410 are included that allow the jacket 200 to be peeled away, yet provide a uniform wall thickness. In this arrangement, the undercuts 410 tend to force separation at the point where guide lumen wall 404 meets the inflation lumen wall(s) 406. In FIG. 4C, the undercuts 410 are eliminated and replaced by reinforcements 412. In this arrangement, the reinforcements 412 tend to force separation on the guide lumen wall 404 somewhere between inflation lumens 302.

Figure 5A:
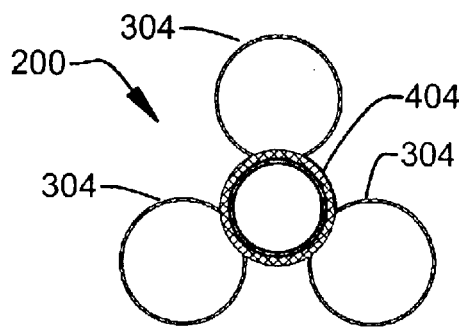
FIG. 5A is a cross sectional view of the outer jacket's inflatable portion corresponding to cross section 5—5 of FIG. 3.

FIG. 5A shows a cross sectional view of the outer jacket 200 at the balloons 304. The balloons 304 (shown inflated) can be either fabricated separately and attached to the guide lumen walls 404 or be molded integral with the walls 404. Although three balloon segments 304 are shown in FIG. 5A, any number of segments could be used depending on the desired effect. A single annular balloon 304 will provide nearly full occlusion of the occupied blood vessel. Use of multiple balloon segments 304, such as shown in FIG. 5A, can provide partial occlusion yet still have a stabilizing effect on the outer jacket 200 in a blood vessel.

Figure 5B:
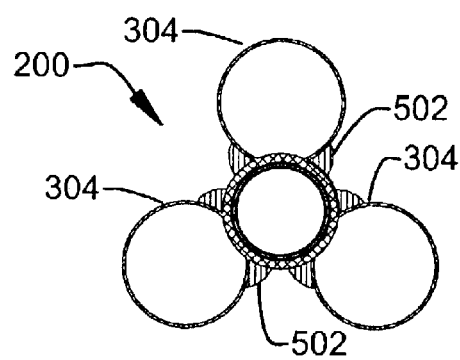
FIG. 5B is a cross sectional view of the outer jacket's inflatable portion corresponding to cross section 5—5 of FIG. 3 showing an alternate arrangement with balloon reinforcements.

As shown in FIG. 5B, excess material can be molded or added to form a thickened region 502 at the base of each balloon lobe. These thickened regions 504 will provide additional longitudinal stiffness to the deflated jacket 200, facilitating advancement of the jacket 200. Also, the thickened regions 502 and reinforcements/undercuts 412, 410 along the inflation lumens 302 will form "rip cords" to aid in peeling the jacket 200 off of the pacing lead.

Figure 6:
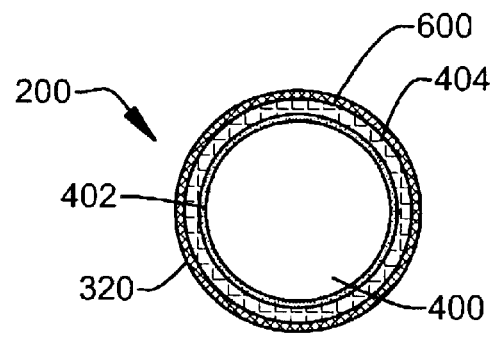
FIG. 6 is a cross sectional view of the outer jacket's distal end corresponding to cross section 6—6 of FIG. 3.

FIG. 6 shows a cross section of the outer jacket 200 at the distal tip 320. The tip 320 may be formed by a soft outer covering 600 bonded over the guide lumen wall 404. The soft outer covering 600 is typically a low durometer material compatible with the guide lumen wall 404 material. Alternatively, the guide lumen wall 404 may already be formed from a sufficiently soft material so that there is no need for a separate covering 600 to enclose the distal tip 320.

Figure 7:
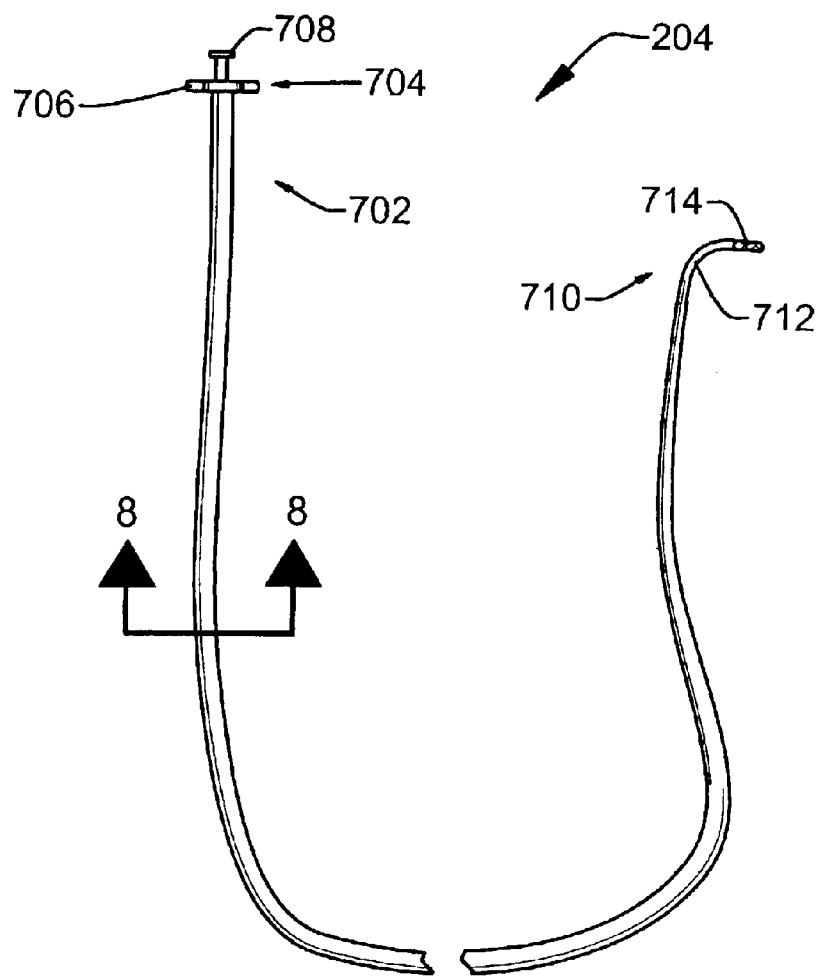
FIG. 7 is a side view of a torquable stylet according to an embodiment of the present invention.

Referring now to FIG. 7, the stylet 204 is illustrated according to one embodiment of the present invention. A hub 704 is attached at the proximal end 702 of the stylet 204. The hub 704 may include protrusions (wings) 706 to allow torquing of the stylet 204 at the proximal end 702. A luer 708 is also shown at the stylet's proximal end 702. The luer 708 allows connection of an RHV type device for guidewire access and for flushing of the stylet 204. Alternatively, separate flush and guidewire luers can be provided as shown on the outer jacket 200 in FIG. 3.

The stylet 204 is typically designed to be smaller and more flexible at the distal end 710 than at the proximal end 702. The distal end 710 of the stylet 204 may include a preformed bend 712 and a soft tip 714. The preformed bend 712 can be thermoset in the stylet during fabrication. The soft tip 714 can be molded or bonded to the stylet 204, preferably so that the distal end 710 maintains a smooth outer profile.

Figure 8:
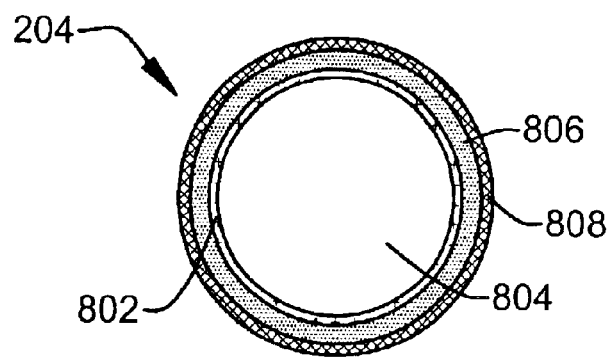
FIG. 8 is a cross sectional view of the torquable stylet corresponding to section 8—8 of FIG. 7.

FIG. 8 shows a cross-section of the stylet 204. The stylet 204 can be constructed to include features of a standard guiding catheter, which usually includes an inner liner 802 surrounding an open lumen 804, a braided composite layer 806, and an outer jacket 808. The inner liner 802 and outer jacket 808 can be made of a lubricious material, typically polyethylene or polytetrafluoroethylene (PTFE). The braided composite layer 806 includes a stainless steel woven braid that provides torsional stiffness to the stylet 204. The composite layer 806 may include the braid alone, or the braid may be molded within a plastic tube which is then sandwiched between the inner liner 802 and outer jacket 808. The braid angles and composite materials of the composite layer may be varied along the length of the stylet 204 to provide for greater stiffness in the proximal end 702 than in the distal end 710.

Figure 9:
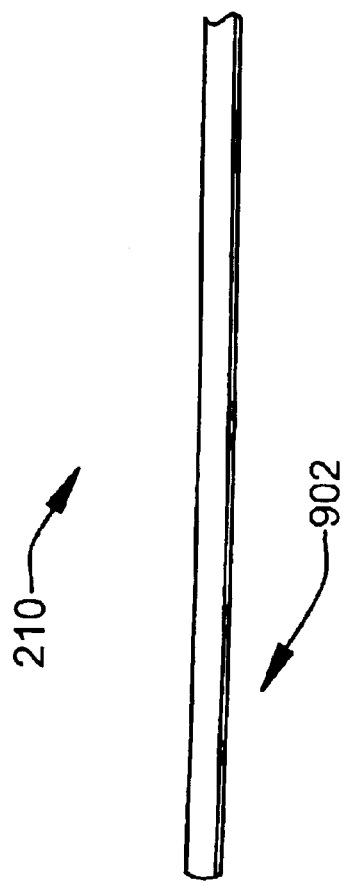
FIG. 9 is a side view of a steerable guidewire with a loop tip according to an embodiment of the present invention.
Figure 9:
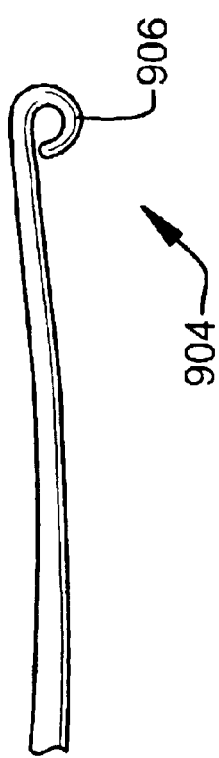

Turning now to FIG. 9, a guidewire 210 is shown according to one embodiment of the present invention. The guidewire has with a flexible distal section 902 and a stiffer proximal section 904. The distal section 902 has a loop tip 906. The loop tip 906 has a diameter ranging from approximately 2 mm to 7 mm. The guidewire 210 can be manufactured from nitinol with a transition temperature such that the loop tip 906 is straight at room temperature and assumes the illustrated shape at body temperature.

Figure 10:
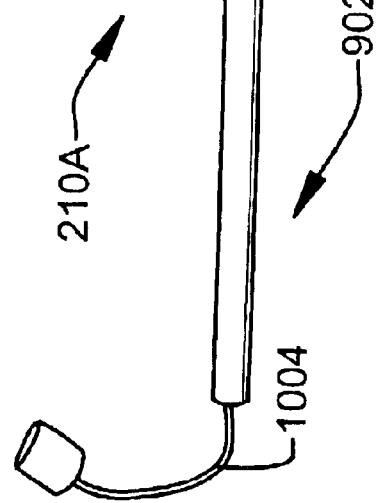
FIG. 10 is a side view of a steerable guidewire with a distally mounted sensor according to an embodiment of the present invention.
Figure 10:
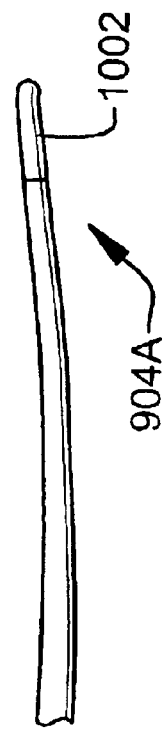

FIG. 10 shows an alternate embodiment of a guidewire 210A incorporating one or more electrical sensors 1002 at the distal end 904A. The electrical sensor 1002 usually includes an electrode, although in some cases another type of sensor may be employed, such as a thermocouple or microelectromechanical system (MEMS) sensor for measuring flow, temperature, pressure, etc. One or more detachable leads 1004 are included at the proximal end 902A for connecting the sensor 1002 to external equipment.

A guide catheter system according to the present invention is particularly useful for facilitating placement of devices into destination vessels, typically cardiac vessels. A particularly appropriate use of such a catheter system is to introduce pacing leads through the vasculature and into the coronary sinus. From the coronary sinus, the pacing leads are implanted into the veins on the left side of the heart. Pacing leads are often implanted in the left heart to treat congestive heart failure (CHF).

The guide catheter system 100 can access the coronary sinus for pacing lead implantation as illustrated in FIG. 1. According to one approach, the outer jacket 200 and stylet 204 are introduced through a puncture or incision 120 into a relatively large access vessel such as the cephalic or subclavian veins. The outer jacket 200 and stylet 204 can, for example, be advanced through the access vessel into the superior vena cava 106 and are thereby moved into the right atrium 104 of the heart. The stylet 204 can be manipulated (e.g., rotated) within the outer jacket 200 to steer and improve advancement of the outer jacket 200.

If the loop-tip guidewire 210 as shown in FIG. 9 is being used, the guidewire 210 and stylet 204 are manipulated together such that the loop tip 906 of the guidewire 210 drags across the wall of the atrium 104. The loop tip 906 is designed to catch as it passes the ostium of the coronary sinus 108, providing tactile feedback to the physician. Once the ostium is located, the guidewire 210 is advanced into the coronary sinus 108 until the loop tip 906 engages the vessel walls and anchors the wire 210.

If the sensor-tipped guidewire 210A as shown in FIG. 10 is being used, the lead 1004 is attached to the proximal end of the guidewire 210A and connected to appropriate monitoring equipment (not shown). The guidewire 210A is advanced until it touches the atrial wall, and the electrical signals are used to determine the likely location of the coronary sinus 108. Once the wire enters the coronary sinus, it is advanced into the sinus 108 to anchor the distal tip of the guidewire 210A.

After the guidewire 210, 210A has been properly anchored, the outer jacket 200 is advanced over the stylet 204 and over the guidewire 210A until the outer jacket 200 enters the coronary sinus 108. If necessary, the stylet 204 may be manipulated (e.g., rotated) to improve access to the coronary sinus 108. In rare cases, it may be necessary to exchange the stylet 204 (leaving the outer jacket 200 and guidewire 210A in place) to substitute a more optimally shaped stylet 204 for accessing the ostium of the coronary sinus.

Having positioned the outer jacket 200 in the coronary sinus 108, the balloon(s) 304 is/are inflated. The distal balloon 304 serves two functions when inflated. First, the balloon 304 aids in anchoring the jacket 200 in the coronary sinus. Second, the balloon 304 provides some restriction to blood flow, improving the quality of retrograde die injections into the coronary veins. When using lobed shaped balloons 304, however, the inflated lobes do not fully occlude the coronary sinus 108, which is advantageous in some situations. The lobed balloons 304 also allow for the balloon section to be relatively long, making the exact positioning of the jacket 200 less significant.

Inflating the balloon(s) 304 also serves to pressurize the inflation lumens 302 arrayed around the outer jacket 200 (best seen in FIG. 4). The pressurization of the inflation lumens 302 will increase the overall stiffness of the outer jacket 200 (thus the term variable stiffness jacket/sheath). The increased overall stiffness will enhance the performance of the jacket 200 when a pacing lead is advanced through it. If additional stiffness is required, the jacket 200 can be designed such that the inflation lumens 304 have thin walls at various portions to serve as small balloons. These proximal balloons enhance the stiffness of the inflated jacket without stiffening the deflated jacket 200.

Once the balloons 304 are inflated, thereby stabilizing and stiffening the outer jacket 200, the stylet 204 and guidewire 210, 210A can be removed. A pacing lead and, if desired, a smaller, more flexible guidewire can then be inserted into the outer jacket 200, through the coronary sinus, and into the proper position in the coronary veins.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A guiding catheter system for accessing a patient's heart, comprising:
    an outer jacket, comprising:
        an open guide lumen extending from a proximal tip of the outer jacket to a distal tip of the outer jacket;
        at least one inflation lumen provided along an exterior surface of the outer jacket; and
        at least one segment of a distal balloon fixably mounted at a distal portion of the outer jacket, the distal balloon in fluid communication with the at least one inflation lumen; and
    a stylet disposed within the guide lumen of the outer jacket and comprising a distal pre-formed bend, the stylet rotatable within the outer jacket along a longitudinal axis of the outer jacket, the distal pre-formed bend of the stylet dimensioned to deflect the outer jacket laterally of the longitudinal axis of the outer jacket upon rotation of the stylet.

2. The guiding catheter system of claim 1, wherein the outer jacket further comprises a peel away feature provided along a longitudinal length of the outer jacket.

3. The guiding catheter system of claim 2, wherein the peel away feature comprises an undercut between the at least one inflation lumen and the exterior surface of the outer jacket.

4. The guiding catheter system of claim 2, wherein the peel away feature comprises a thickened section at an interface between the at least one inflation lumen and the exterior surface of the outer jacket.

5. The guiding catheter system of claim 1, wherein the stylet comprises an open lumen, the guiding catheter system further comprising a guidewire movably disposed within the open lumen of the stylet.

6. The guiding catheter system of claim 5, wherein the guidewire comprises a loop at a distal tip of the guidewire.

7. The guiding catheter system of claim 5, wherein the guidewire is formed from a material such that a distal tip of the guidewire is substantially straight at ambient temperature and the distal tip assumes a shape of a loop at body temperature.

8. The guiding catheter system of claim 5, wherein the guidewire comprises a sensor at a distal tip of the guidewire.

9. The guiding catheter system of claim 8, wherein the sensor comprises an electrode.

10. The guiding catheter system of claim 1, wherein the open guide lumen of the outer jacket is dimensioned to receive a medical electrical lead.

11. The guiding catheter system of claim 1, further comprising one or more secondary balloons integrated into the inflation lumen, the secondary balloons proximal to the distal balloon segment.

12. A method of cannulating a destination blood vessel, comprising:
    introducing an outer jacket and a stylet of a catheter system into an access vessel, the outer jacket comprising a guide lumen extending from a proximal tip of the outer jacket to a distal tip of the outer jacket;
    rotating the stylet within the guide lumen of the outer jacket so that a pre-formed bend on a distal end of the stylet deflects the outer jacket to steer a distal end of the outer jacket;
    advancing a guidewire through an open lumen of the stylet to engage the destination blood vessel with a distal end of the guidewire; and
    inflating a balloon attached to a distal portion of the outer jacket to engage a portion of the access vessel or the destination blood vessel with the outer jacket.

13. The method of claim 12, wherein engaging the destination vessel with a distal end of the guidewire further comprises using a sensor disposed at the distal end of the guidewire to direct the distal end of the guidewire to the destination blood vessel.

14. The method of claim 13, wherein the sensor comprises an electrode.

15. The method of claim 12, further comprising advancing the outer jacket over the guidewire after the distal end of the guidewire has engaged the destination blood vessel to seat the outer jacket in the destination blood vessel.

16. The method of claim 12, further comprising removing the guidewire and stylet after seating the outer jacket in a destination blood vessel.

17. The method of claim 16, further comprising advancing an electrical medical lead through the outer jacket for passage into or through the destination blood vessel.

18. The method of claim 16, further comprising advancing an electrical medical lead through the outer jacket for passage into or through a left heart blood vessel or a left heart chamber.

19. The method of claim 12, wherein engaging a portion of the access vessel with the outer jacket further comprises inflating a second balloon attached to the outer jacket proximal to the balloon at the distal end.

20. A guiding catheter system for accessing a patient's head, comprising:
    an outer jacket having an open guide lumen and a plurality of fluted balloons fixably mounted at a distal portion of the outer jacket, the open guide lumen extending from a proximal tip of the outer jacket to a distal tip of the outer jacket, each of the fluted balloons fluidly coupled to an inflation lumen provided along a length of the outer jacket;
    a stylet disposed within the guide lumen of the outer jacket, the stylet rotatable within the outer jacket along a longitudinal axis of the outer jacket, the stylet comprising an open lumen; and a guidewire movably disposed within the open lumen of the stylet.

21. The guiding catheter system of claim 20, wherein the outer jacket further comprises a peel away feature provided along a longitudinal length of the outer jacket.

22. The guiding catheter system of claim 20, wherein the guidewire is formed from a material such that a distal tip of the guidewire is substantially straight at ambient temperature and the distal tip assumes a shape of a loop at body temperature.

23. The guiding catheter system of claim 20, wherein the guidewire comprises a sensor at a distal tip of the guidewire.

24. The guiding catheter system of claim 20, wherein the stylet comprises a pre-formed curve at a distal portion of the stylet, the pre-formed curve dimensioned to impart a deflection to the outer jacket.

25. The guiding catheter system of claim 20, further comprising one or more secondary balloons integrated into the inflation lumen, the secondary balloons proximal to the fluted balloons.

* * * * *

UNITED STATES PATENT AND TRADEMARK OFFICE
CERTIFICATE OF CORRECTION

PATENT NO. : 6,928,313 B2
DATED : August 9, 2005
INVENTOR(S) : Peterson

It is certified that error appears in the above-identified patent and that said Letters Patent is hereby corrected as shown below:

Column 8,
Line 58, "head" should read -- heart --.

Signed and Sealed this

Twenty-seventh Day of December, 2005

JON W. DUDAS
*Director of the United States Patent and Trademark Office*